United States Patent
Chen et al.

(10) Patent No.: US 11,598,763 B2
(45) Date of Patent: Mar. 7, 2023

(54) RECONFIGURABLE MEASUREMENT SYSTEM

(71) Applicant: Ascensia Diabetes Care Holdings AG, Basel (CH)

(72) Inventors: Jun Chen, Warren, NJ (US); Christopher A. Dionisio, Millington, NJ (US)

(73) Assignee: Ascensia Diabetes Care Holdings AG, Basel (CH)

(*) Notice: Subject to any disclaimer, the term of this patent is extended or adjusted under 35 U.S.C. 154(b) by 505 days.

(21) Appl. No.: 15/502,381

(22) PCT Filed: Aug. 4, 2015

(86) PCT No.: PCT/US2015/043579
§ 371 (c)(1),
(2) Date: Feb. 7, 2017

(87) PCT Pub. No.: WO2016/025236
PCT Pub. Date: Feb. 18, 2016

(65) Prior Publication Data
US 2017/0235911 A1    Aug. 17, 2017

Related U.S. Application Data

(60) Provisional application No. 62/035,899, filed on Aug. 11, 2014.

(51) Int. Cl.
*G01N 33/487* (2006.01)
*G16H 40/40* (2018.01)
(Continued)

(52) U.S. Cl.
CPC ....... *G01N 33/48792* (2013.01); *G01N 33/49* (2013.01); *G16H 10/60* (2018.01);
(Continued)

(58) Field of Classification Search
None
See application file for complete search history.

(56) References Cited

U.S. PATENT DOCUMENTS

5,366,609 A * 11/1994 White .............. G01N 33/48792
204/403.04
8,216,138 B1 * 7/2012 McGarraugh ...... A61B 5/14532
600/365
(Continued)

FOREIGN PATENT DOCUMENTS

EP       2040065 A1 *  3/2009  ............. G01N 27/26
WO  WO2008097316 A1 *  8/2008  ............. G06F 21/00
(Continued)

OTHER PUBLICATIONS

Zawn Villines, "What to know about fasting blood sugar?" https://www.medicalnewstoday.com/articles/317466 Mar. 22, 2019 (Year: 2019).*
(Continued)

*Primary Examiner* — Paul R Fisher
(74) *Attorney, Agent, or Firm* — Erise IP, P.A.

(57) ABSTRACT

A system for measuring health data includes a measurement device. The measurement device includes at least one measurement interface to receive a first fluid sample, a processor to measure one or more first characteristics of the first fluid sample, and at least one memory device to store first data. The processor reads the first data and measures the one or more first characteristics of the first fluid sample according to the first data. The at least one memory device also stores second data. The processor reads the second data instead of the first data to reconfigure the measurement device and measures one or more second characteristics of a second fluid sample according to the second data. An external processing device may be communicatively coupled to the measurement device and may execute a healthcare applica-
(Continued)

tion that communicates with the measurement device and may be employed to reconfigure the measurement device.

20 Claims, 5 Drawing Sheets

(51) Int. Cl.
G16H 40/67 (2018.01)
G16H 10/60 (2018.01)
G01N 33/49 (2006.01)
A61B 5/145 (2006.01)
A61B 5/00 (2006.01)
A61B 5/1455 (2006.01)
A61B 5/1495 (2006.01)

(52) U.S. Cl.
CPC ............ G16H 40/40 (2018.01); G16H 40/67 (2018.01); A61B 5/0024 (2013.01); A61B 5/1495 (2013.01); A61B 5/14542 (2013.01); A61B 5/14551 (2013.01); A61B 5/6898 (2013.01); A61B 5/72 (2013.01)

(56) References Cited

U.S. PATENT DOCUMENTS

| | | | | |
|---|---|---|---|---|
| 2003/0083686 | A1* | 5/2003 | Freeman | A61B 5/15178 606/181 |
| 2004/0186365 | A1* | 9/2004 | Jin | A61B 5/14532 128/903 |
| 2005/0143675 | A1* | 6/2005 | Neel | A61B 5/15113 600/583 |
| 2006/0051738 | A1* | 3/2006 | Zweig | C12Q 1/005 435/4 |
| 2008/0300919 | A1* | 12/2008 | Charlton | A61B 5/14532 705/2 |
| 2011/0213225 | A1 | 9/2011 | Bernstein | |
| 2012/0100887 | A1* | 4/2012 | Tekin | G16H 40/67 455/556.1 |
| 2012/0245439 | A1 | 9/2012 | Andre | |
| 2013/0012796 | A1* | 1/2013 | Kak | A61B 5/6898 600/365 |
| 2013/0066644 | A1* | 3/2013 | Dicks | A61B 5/0022 705/2 |
| 2013/0265054 | A1* | 10/2013 | Lowery, Jr. | G01R 33/281 324/319 |

FOREIGN PATENT DOCUMENTS

| | | | | |
|---|---|---|---|---|
| WO | WO 2009/029453 | A2 | 3/2009 | |
| WO | WO2010117820 | A2 * | 10/2010 | ............. A61G 7/14 |
| WO | WO 2013/086363 | A2 | 6/2013 | |
| WO | WO 2013/140163 | A1 | 9/2013 | |

OTHER PUBLICATIONS

Children with Diabetes, "Diagnosis and Symptoms" https://childrenwithdiabetes.com/question/although-my-daughters-fasting-glucose-test-was-normal-i-have-seen-post-meal-numbers-as-high-as-171-mg-dl-9-5-mmol-l-per-my-husbands-meter-what-does-this-mean-could-she-have-enough-insulin-to-m/ Feb. 23, 2008 (Year: 2008).*
Roche Diagnostics, "Accutrend Plus User's Manual", https://beta-static.fishersci.com/content/dam/fishersci/en_US/documents/programs/healthcare/technical-documents/user-manuals/roche-accutrend-plus-users-manual.pdf, 2012 (Year: 2012).*
Jeffrey D. Newman, Anthony P.F. Turner, "Home blood glucose biosensors: a commercial perspective", Biosensors and Bioelectronics, vol. 20, Issue 12, 2005, pp. 2435-2453. (Year: 2005).*
MediSense, "Precision Xtra User's Guide" https://www.betterlivingnow.com/images/products/itmmmImages/57599881401-2.PDF 2005 (Year: 2005).*
Diabeteswellbeing.com, "Precision Xtra Blood Glucose Meter Review", https://diabeteswellbeing.com/precision-xtra-blood-glucose-meter-review/, Jun. 29, 2013. (Year: 2013).*
J. Ko, C. Lu, M. B. Srivastava, J. A. Stankovic, A. Terzis and M. Welsh, "Wireless Sensor Networks for Healthcare," in Proceedings of the IEEE, vol. 98, No. 11, pp. 1947-1960, Nov. 2010, doi: 10.1109/JPROC.2010.2065210. (Year: 2010).*
Lynne T. Harris et al., Designing mobile support for glycemic control in patients with diabetes, Journal of Biomedical Informatics, vol. 43, Issue 5, Supplement, 2010, pp. S37-S40 (Year: 2010).*
W. Zhang et al. , "A secure and scalable telemonitoring system using ultra-low-energy wireless sensor interface for long-term monitoring in life science applications," 2013 IEEE International Conference on Automation Science and Engineering (CASE), 2013, pp. 617-622, doi: 10.1109/CoASE.2013.6653979 (Year: 2013).*
Noel Baisa, "Designing wireless interfaces for patient monitoring equipment", Medical Electronics, www.rfdesign.com, Apr. 2005 (Year: 2005).*
Landolsi, Taha, Abdul-Rahman Al-Ali, and Yousef Al-Assaf. "Wireless Stand-alone Portable Patient Monitoring and Logging System." J. Commun. 2.4 (2007): 65-70. (Year: 2007).*
European Patent Office, International Search Report and Written Opinion of International Searching Authority for PCT/US2015/043579, dated Oct. 29, 2015 (18 pages).
Nemiroski, A. et al., "Universal mobile electrochemical detector designed for use in resource-limited applications," Proceedings of the National Academy of Sciences, 111(33): 11984-11989, Aug. 4, 2014.
Extended European Search Report in European Patent Application No. EP 20180764.1, dated Jan. 20, 2021 (9 pages).
European Patent Office, Examination Report, Application No. 20180764.1-1203, dated Dec. 5, 2022.

* cited by examiner

RECONFIGURABLE MEASUREMENT SYSTEM

CROSS REFERENCE TO RELATED APPLICATIONS

This application is a National Stage of International Application No. PCT/US2015/043579, filed Aug. 4, 2015, which claims priority to and the benefit of U.S. Provisional Patent Application No. 62/035,899, filed on Aug. 11, 2014, each of which is hereby incorporated by reference herein in its entirety.

FIELD OF THE INVENTION

The present invention relates generally to systems and methods for measuring health data. More specifically, the present invention relates to systems and methods that employ a measurement device that can be reconfigured according to selected data that determines how the measurement device operates.

BACKGROUND OF THE INVENTION

The quantitative determination of analytes in body fluids is of great importance in the diagnoses and maintenance of certain physiological conditions. For example, persons with diabetes (PWDs) frequently check the glucose level in their bodily fluids. The results of such tests can be used to regulate the glucose intake in their diets and/or to determine whether insulin or other medication needs to be administered.

A PWD typically uses a measurement device (e.g., a blood glucose meter) that calculates the glucose concentration in a fluid sample from the PWD. The measurement device operates by measuring a raw electrochemical or optical signal from a reaction between a reagent and the glucose in the sample. Currently, electrochemical or optical measurement devices are designed and programmed to employ a hardcoded measurement sequence to obtain the raw signal. The measurement devices then use a calculation sequence to process the raw signal data according to a hardcoded algorithm. The measurement sequence instructs the measurement device how to perform the actual measurement electrochemically or optically and how to obtain an electrochemical or optical signal as raw measurement data. The calculation sequence instructs the measurement device how to convert the raw measurement data into a final measurement value (e.g., blood glucose concentration expressed as milligrams per deciliter (mg/dL)) that can be communicated to the PWD. The measurement sequence and calculation sequence are hardcoded into the measurement device, and the measurement device is limited to operating according to these specific sequences.

SUMMARY

In view of the foregoing, even a slight change to the measurement sequence or calculation sequence in a hardcoded measurement device requires the measurement device to be completely reprogrammed in a process that is typically time consuming, expensive, and often impractical or unfeasible. To address the limitations of using a hardcoded measurement device, embodiments of the present invention employ a measurement device that can be easily reconfigured to use a selected measurement sequence, calculation sequence, and/or other data that determines how the measurement device operates. In some cases, the measurement device may be reconfigured to use a measurement sequence or a calculation sequence that includes updated instructions, e.g., with bug fixes or enhancements. Advantageously, the measurement device can be reconfigured to conduct a plurality of chemistry measurements, i.e., to support multiple different algorithms as well as measurement of different types of health data (blood glucose, $A_{1C}$, cholesterol, coagulation (PT/INR), etc.).

According to some embodiments, a system for measuring health data includes a measurement device. The measurement device includes at least one measurement interface configured to receive a first fluid sample, a processor configured to measure one or more first characteristics of the first fluid sample received by the at least one measurement interface, and at least one memory device configured to store first data. The processor reads the first data and measures the one or more first characteristics of the first fluid sample according to the first data. The at least one memory device is further configured to store second data. The processor reads the second data instead of the first data to reconfigure the measurement device and measures one or more second characteristics of a second fluid sample according to the second data. The second fluid sample is received by the at least one measurement interface. The system may also include an external processing device configured to be communicatively coupled to the measurement device and to execute a healthcare application that communicates with the measurement device.

In some cases, the measurement device may further include an analog front end coupled to the at least one measurement interface and the processor. The first data may include a first measurement sequence and the second data may include a second measurement sequence. The analog front end may be configured to receive a first raw measurement signal from the at least one measurement interface according to the first measurement sequence. When the measurement device is reconfigured, the analog front end may be configured to receive a second raw measurement signal from the at least one measurement interface according to the second measurement sequence. In addition, an external processing device may be communicatively coupled to the measurement device and to execute a healthcare application that communicates with the measurement device. The measurement device may send the first raw measurement signal or the second raw measurement signal to the healthcare application. The external processing device may store a first calculation sequence or a second calculation sequence. The healthcare application may convert the first raw measurement signal or the second raw measurement signal to a measurement value according to the first calculation sequence or the second calculation sequence, respectively. The healthcare application may display the measurement value on a display of the external processing device.

In other cases, the first data may also include a first calculation sequence and the second data may include a second calculation sequence. The processor may be configured to convert the first raw measurement signal to a measurement value according to the first calculation sequence. When the measurement device is reconfigured, the processor may be configured to convert the second raw measurement signal to a measurement value according to the second calculation sequence. In addition, an external processing device may be communicatively coupled to the measurement device and to execute a healthcare application that communicates with the measurement device. The measurement device may send the measurement value to the healthcare application. The healthcare application may display the measurement value on a display of the external processing device.

In further cases, the at least one measurement interface may include a plurality of measurement interfaces, and the measurement device is configured to receive a fluid sample via any one of the measurement interfaces. The first data may configure the measurement device to receive the first fluid sample via one of the measurement interfaces and the second data may configure the measurement device to receive the second fluid sample via another of the measurement interfaces.

Still other aspects, features, and advantages of the present invention are readily apparent from the following detailed description, by illustrating a number of exemplary embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive. The invention is to cover all modifications, equivalents, and alternatives falling within the spirit and scope of the invention.

DETAILED DESCRIPTION

To address the limitations of using a hardcoded measurement device, embodiments of the present invention employ a measurement device that can be easily reconfigured to use a selected measurement sequence, calculation sequence, and/or other data that determines how the measurement device operates. In some cases, the measurement device may be reconfigured to use a measurement sequence or a calculation sequence that includes updated instructions, e.g., with bug fixes or enhancements. Advantageously, the measurement device can be reconfigured to conduct a plurality of chemistry measurements, i.e., to support multiple different algorithms as well as measurement of different types of health data (blood glucose, $A_{1C}$, cholesterol, coagulation (PT/INR), etc.).

Figure 1:
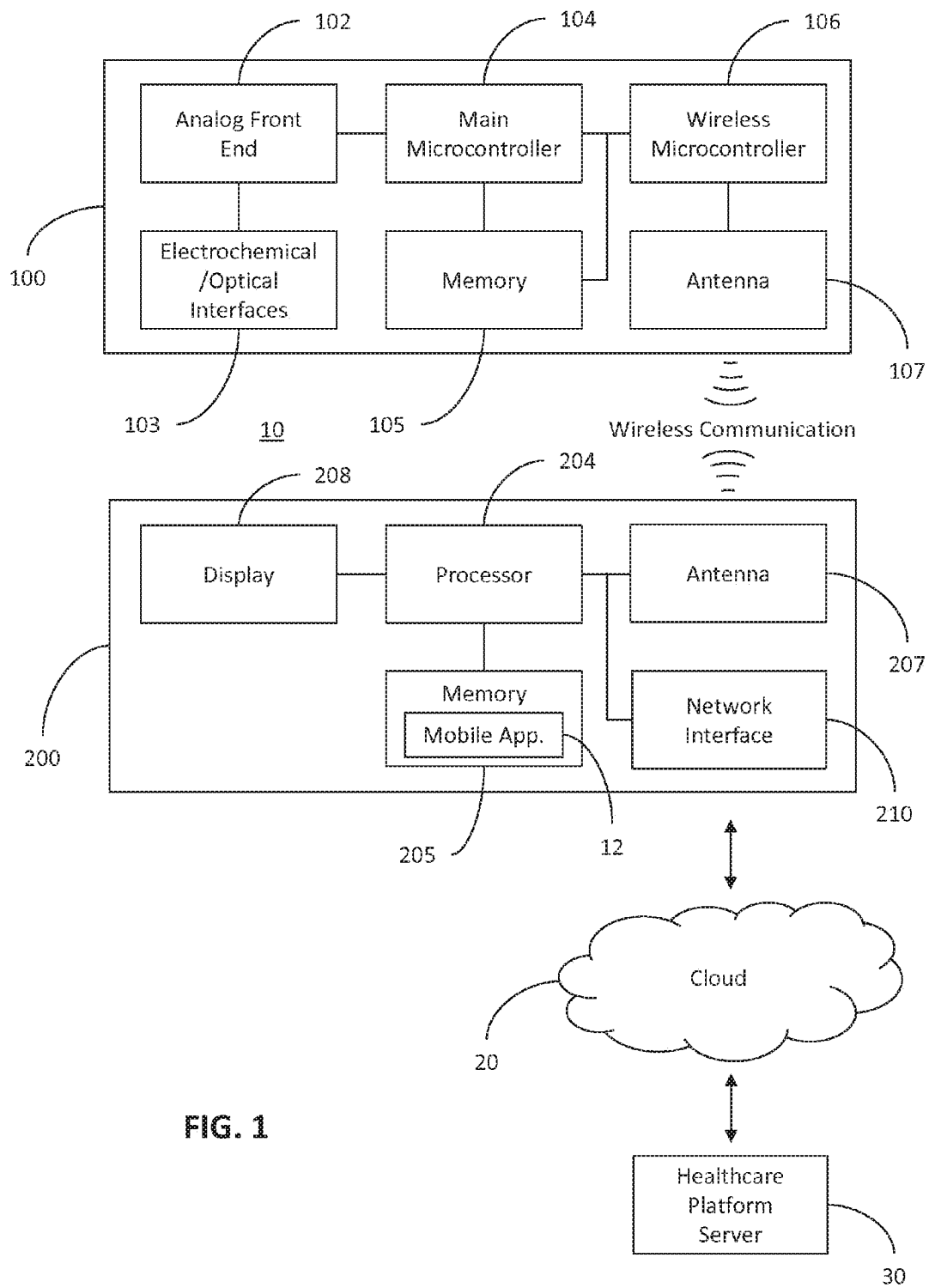
FIG. 1 illustrates an example system employing a reconfigurable measurement device according to aspects of the present invention.

Referring to FIG. 1, an example system 10 employing a reconfigurable measurement device 100 and an external processing device 200 is illustrated. In particular, the measurement device 100 includes an analog front end 102, at least one measurement interface 103, a main microcontroller 104, a memory 105, a wireless microcontroller 106, and an antenna 107.

The analog front end 102 is coupled to the at least one measurement interface 103, which includes hardware to receive a fluid sample directly or indirectly. In some embodiments, for example, the measurement device 100 measures the concentration of an analyte in the fluid sample. The fluid sample may include, for example, a whole blood sample, a blood serum sample, a blood plasma sample, other body fluids like ISF (interstitial fluid), saliva, and urine, as well as non-body fluids. Analytes that may be analyzed include glucose, lipid profiles (e.g., cholesterol, triglycerides, LDL and HDL), microalbumin, hemoglobin $A_{1C}$, fructose, lactate, or bilirubin. In general, aspects of the present invention may be employed to measure one or more characteristics of a sample, such as analyte concentration, enzyme and electrolyte activity, antibody titer, etc.

In some embodiments, the at least one measurement interface 103 includes a port that receives a test sensor (not shown) configured to receive the fluid sample directly. For example, a user may employ a lancing device to pierce a finger or other area of the body to produce a blood sample at the skin surface. The user may then collect this blood sample by placing the test sensor into contact with the sample. The test sensor contains a reagent which reacts with the sample to indicate the concentration of an analyte in the sample. In engagement with the test sensor, the at least one measurement interface 103 allows the reaction to be measured by the analog front end 102.

In some cases, the test sensor may be an electrochemical test sensor. An electrochemical test sensor typically includes a plurality of electrodes and a fluid-receiving area that receives the fluid sample and includes appropriate reagent(s) (e.g., enzyme(s)) for converting an analyte of interest (e.g., glucose) in a fluid sample (e.g., blood) into a chemical species that produces an electrical current which is electrochemically measurable by the components of the electrode pattern. In such cases, the respective measurement interface 103 allows the analog front end 102 to be coupled to the electrodes of the test sensor, and the analog front end 102 receives a raw signal from the respective measurement interface 103.

In other cases, the test sensor may be an optical test sensor. Optical test sensor systems may use techniques such as transmission spectroscopy, diffuse reflectance, or fluorescence spectroscopy for measuring the analyte concentration. For example, an indicator reagent system and an analyte in a sample of body fluid can be reacted to produce a chromatic reaction, as the reaction between the reagent and analyte causes the sample to change color. The degree of color change is indicative of the analyte concentration in the body fluid. The color change of the sample can be evaluated to measure the absorbance level of a transmitted light. In such cases, the respective measurement interface 103 allows a light to be transmitted to the test sensor and the analog front end 102 to receive a raw optical signal based on the light absorbed by, and reflected from, the fluid sample on the test sensor.

In general, the analog front end 102 is employed to measure characteristic(s) of fluid samples received via the at least one measurement interface 103. It is understood that any number of measurement interfaces 103 (electrochemical, optical, etc.) may be coupled to the analog front end 102 to obtain any type of raw signal that can be translated into any type of measurement data.

Also coupled to the analog front end 102, the main microcontroller 104 controls operative aspects of the measurement device 100 as described further below. For example, the main microcontroller 104 can manage the measurement sequence that determines how the actual electrochemical or optical measurement is performed and how the raw electrochemical or optical signal is obtained by the analog front end 102 from the respective measurement interface 103. In addition, the main microcontroller 104 can determine how the raw signal received by the analog front end 102 is converted with a calculation sequence into a final measurement value (e.g., blood glucose concentration expressed as milligrams per deciliter (mg/dL)) that can be communicated to the user, e.g., by a display. Although the analog front end 102 and the main microcontroller 104 are shown separately in FIG. 1, it is contemplated that the main microcontroller 104 in alternative embodiments may include a sufficient analog front end to measure characteristic(s) of a fluid sample received via the at least one measurement interface 103. In addition, it is contemplated that the main controller 104 shown in FIG. 1 may generally represent any number and configuration of processing hardware and associated components required to manage the operation of the measurement device 100.

The memory 105 (e.g., non-volatile memory) may include any number of storage devices, e.g., EEPROM, flash memory, etc. The memory 105 may store measurement data. In addition, the memory 105 may store data, e.g., firmware, software, algorithm data, program parameters, calibration data, lookup tables, etc., that are employed in the operation of other components of the measurement device 100.

The measurement device 100 stores firmware on the memory 105, but according to aspects of the present invention, the firmware does not include a hardcoded algorithm. Instead, the firmware can be executed with any selected algorithm data modifiably stored on the memory 105. In other words, the algorithm can be changed dynamically by selecting different algorithm data stored on the memory 105. As such, the firmware essentially acts as an interpreter of algorithm data selected from the memory 105. Reconfiguring the operation of the measurement device 100 only requires modifying the algorithm data used with the firmware and does not require direct changes to the firmware.

For example, the measurement device 100 can be reconfigured to use a different measurement sequence to obtain a raw signal via the at least one measurement interface 103 and/or a different calculation sequence to process the raw signal according to a different algorithm. Because the memory 105 can store any measurement sequence and/or calculation sequence, this solution enables using a single hardware device to support many different algorithms as well as different types of measurements (blood glucose, $A_{1C}$, cholesterol, coagulation (PT/INR), etc.).

Figure 2:
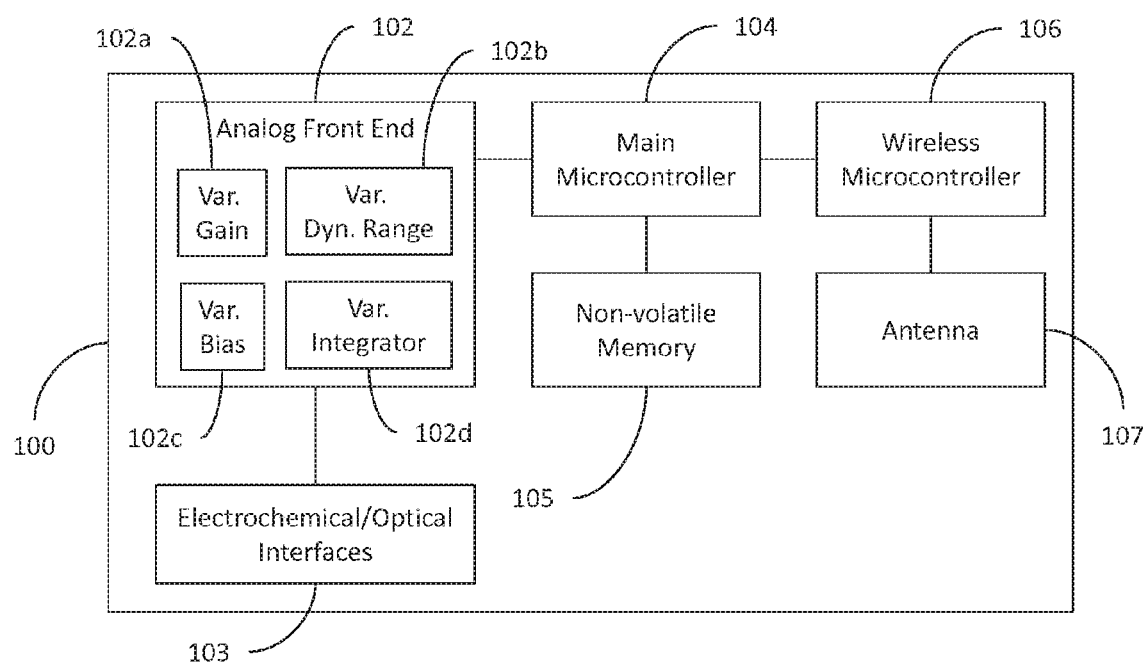
FIG. 2 illustrates further aspects of the reconfigurable measurement device of FIG. 1, according to aspects of the present invention.

For example, FIG. 2 illustrates further aspects of the example measurement device 100. The analog front end 102 as shown in FIG. 2 includes a variable gain 102a, a variable dynamic range 102b, a variable bias 102c, and a variable integrator 102d, all of which are employed to receive and process the raw signal from the at least one measurement interface 103. Any aspect of the operation of the variable components 102a-d of the analog front end 102 can be modified with data stored in the memory 105 to reconfigure the measurement device 100. This data may include new or updated software, algorithm data, program parameters, calibration data, lookup tables, etc., for the operation of the analog front end 102.

As further illustrated in FIG. 1, the measurement device 100 also includes an antenna 107 that allows the measurement device 100 to communicate wirelessly with the external processing device 200. The external processing device 200 may be a smart device, such as a smart telephone, that includes a mobile application that can be paired with the measurement device 100 to provide additional functionality as described further below. In other embodiments, the external processing device 200 may be a tablet computer, a handheld or pocket personal computer, a personal digital assistant (PDA), a desktop or laptop personal computer (PC), or other similar processing/communication devices employing any operating system and communication functions. The measurement device 100 may also include a wireless microcontroller 106 that controls communications through the antenna 107. Although the main microcontroller 104 and the wireless microcontroller 106 are shown separately in FIG. 1, it is contemplated that a common microcontroller in alternative embodiments may be employed to control the wireless communications in addition to other aspects of the measurement device 100.

The external processing device 200 also includes an antenna 207 that allows the external processing device 200 to communicate wirelessly with the measurement device 100. The measurement device 100 and the external processing device 200, for example, may communicate via Bluetooth® wireless technology. In other embodiments, however, communication may be established by other wireless technologies, including near field communication (NFC), radio frequency (RF), personal area network (PAN), Wi-Fi™ (IEEE 802.11), or the like. Alternatively or additionally, communication may be established by wired communication, e.g., universal serial bus (USB).

The external processing device 200 includes a processor 204 that generally controls aspects of the external processing device 200. For example, the processor 204 provides the processing required to run software applications that reside on the external processing device 200. A memory 205 on the external processing device 200 stores the computer-readable instructions for such software applications. The memory 205 may include non-volatile memory, such as flash memory or the like, to store user software applications.

According to aspects of the present invention, the memory 205 stores a healthcare application 12 that complements the operation of the measurement device 100. For example, if the external processing device 200 is a smart device, e.g., a smart telephone, the healthcare application 12 may be a mobile application that is downloaded onto the smart device by the user. In some embodiments, the healthcare application 12 may store and/or process measurements and/or other data communicated wirelessly from the measurement device 100. For example, the healthcare application 12 may statistically analyze the measurement data and provide advanced display of the statistical analysis on a display 208 of the external processing device 200. Indeed, the healthcare application 12 may provide features that are not available through the measurement device 100 alone, particularly because the external processing device 200 may have greater processing and display capabilities than the measurement device 100.

In some embodiments, the healthcare application 12 is employed in a platform for delivering a variety of healthcare services relating to the use of the measurement device 100. For example, a company selling/distributing the measurement device 100 may provide its customers with the healthcare application 12 to provide features and services that enhance the measurement device 100. Because the measurement device 100 can be communicatively coupled to the external processing device 200, aspects of the present invention can employ applications on the external processing device 200 to expand the use of the measurement device 100. For example, the measurement device 100 can be coupled to the external processing device 200 so that the healthcare application 12 residing on the external processing device 200 can be used to reconfigure the measurement device 100 by providing new or updated data for the operation of the measurement device 100 (e.g., new or updated software, algorithm data, program parameters, calibration data, lookup tables, etc.).

As shown in FIG. 1, the external processing device 200 includes a network interface 210 that allows the external processing device 200 to connect to an external network 20. The network interface 210 may employ any technique to connect to the external network 20. For example, the network interface 210 may connect with the external network 20 wirelessly, e.g., Wi-Fi™ (IEEE 802.11), cellular, etc., or via a wired technique, e.g., Ethernet, etc. The external network 20 may be any type of network, e.g., wide-area network (WAN), local-area network (LAN), cloud, etc.

Through the network interface 210, the external processing device 200 may access any resource available through the external network 20. In particular, the external processing device 200 can access resources that relate to the operation of the measurement device 100. As shown in FIG. 1, the external processing device 200 communicates with an external server 30 over the external network 20, shown for example as a cloud network. The external server 30 is related to some healthcare platform that delivers a variety of healthcare services relating to the use of the measurement device 100. For example, the external server 30 may act as the source of the healthcare application 12, which the external processing device 200 can receive over the external network 20 via the network interface 210.

Because the external processing device 200 can be communicatively coupled to resources on an external network 20, the external processing device 200 can generally receive, from any external sources, data that can be used in association with the measurement device 100. Furthermore, because the external processing device 200 can be communicatively coupled to the measurement device 100, the measurement device 100 can in turn receive such data from the external sources. Taking this concept further, the external processing device 200 can be employed to reconfigure the measurement device 100 with data received from external sources, e.g., the healthcare platform server 30, on the external network 20.

For example, the measurement device 100 can be coupled to the external processing device 200 so that the healthcare application 12 on the external processing device 200 can be used to receive new or updated algorithm data from an external source, e.g., the healthcare platform server 30, and to upload this new or updated algorithm data to the memory 105. The operation of the measurement device 100 is then reconfigured when the firmware is executed with the new or updated algorithm data. Allowing a user, e.g., PWD, to connect the measurement device 100 to the external processing device 200 (e.g., wirelessly) and to download data (e.g., algorithm data) requires significantly less manual intervention (e.g., by a manufacturer) to modify the operation of the measurement device 100 in a field upgrade.

Figure 3:
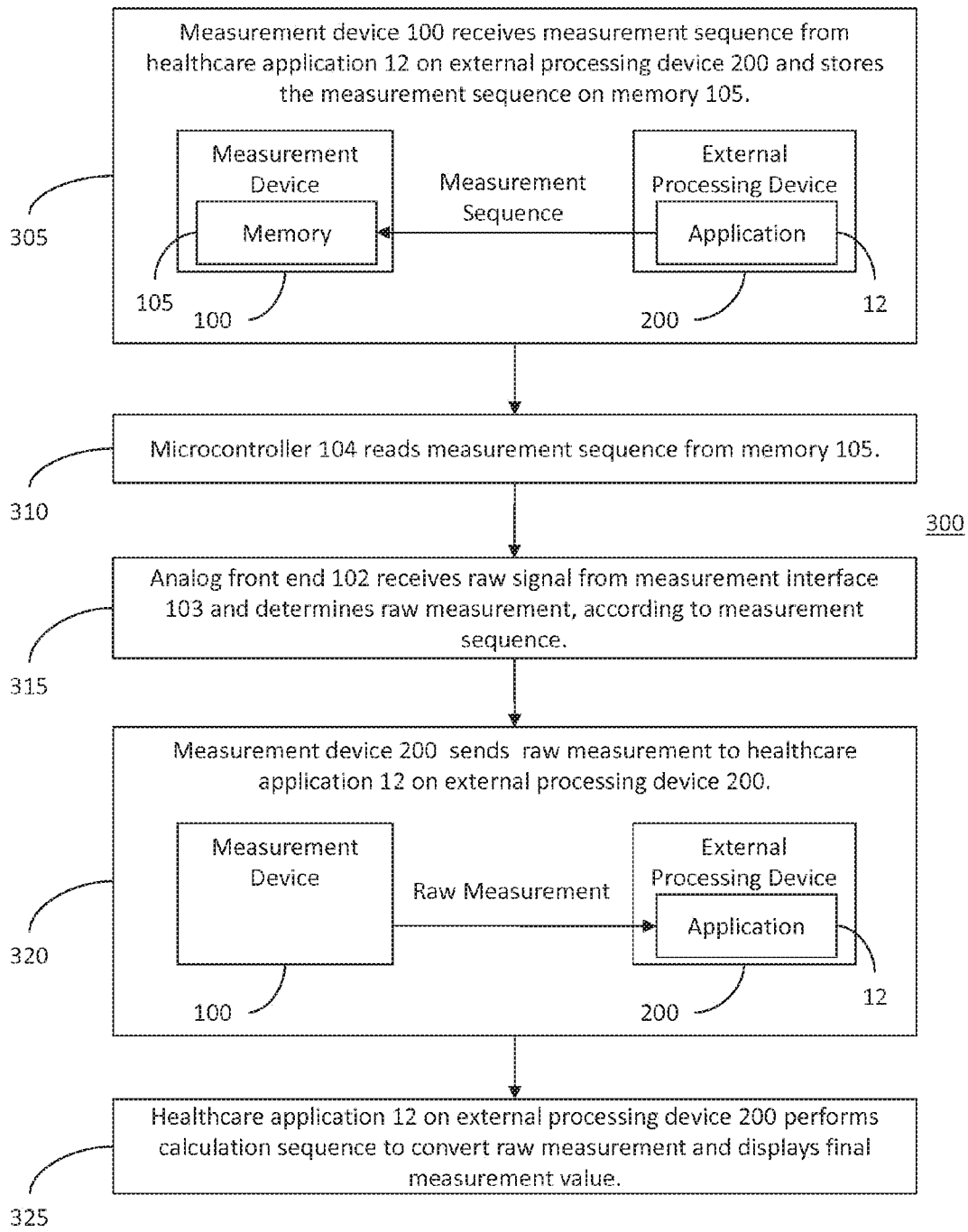
FIG. 3 illustrates an example approach for reconfiguring a measurement device, according to aspects of the present invention.

Employing the external healthcare application 12, the operation of the measurement device 100 can be reconfigured according to different approaches. FIG. 3 illustrates an example approach 300 for reconfiguring the measurement device 100. In act 305, the measurement device 100 receives a measurement sequence from the healthcare application 12 residing on the external processing device 200 and stores the measurement sequence on the memory 105. As described above, the measurement sequence determines how the actual electrochemical or optical measurement is performed with the measurement interface 103 and how the raw electrochemical or optical signal is determined by the analog front end 102. The main microcontroller 104 reads and processes the measurement sequence stored on the memory 105 in act 310. In act 315, the analog front end 102 receives the raw signal from the measurement interface 103 and the raw measurement data is determined according to the measurement sequence. Unlike other embodiments, the measurement device 100 does not process the raw measurement data to determine the final measurement value (e.g., blood glucose concentration expressed as milligrams per deciliter (mg/dL)). Rather, in act 320, the measurement device 100 sends the raw measurement data to the healthcare application 12 residing on the external processing device 200. The external processing device 200 stores a calculation sequence which the healthcare application 12 uses in act 325 to convert the raw measurement data to a final measurement value. The healthcare application 12 communicates the final measurement value to the user, e.g., via the display 208.

Figure 4:
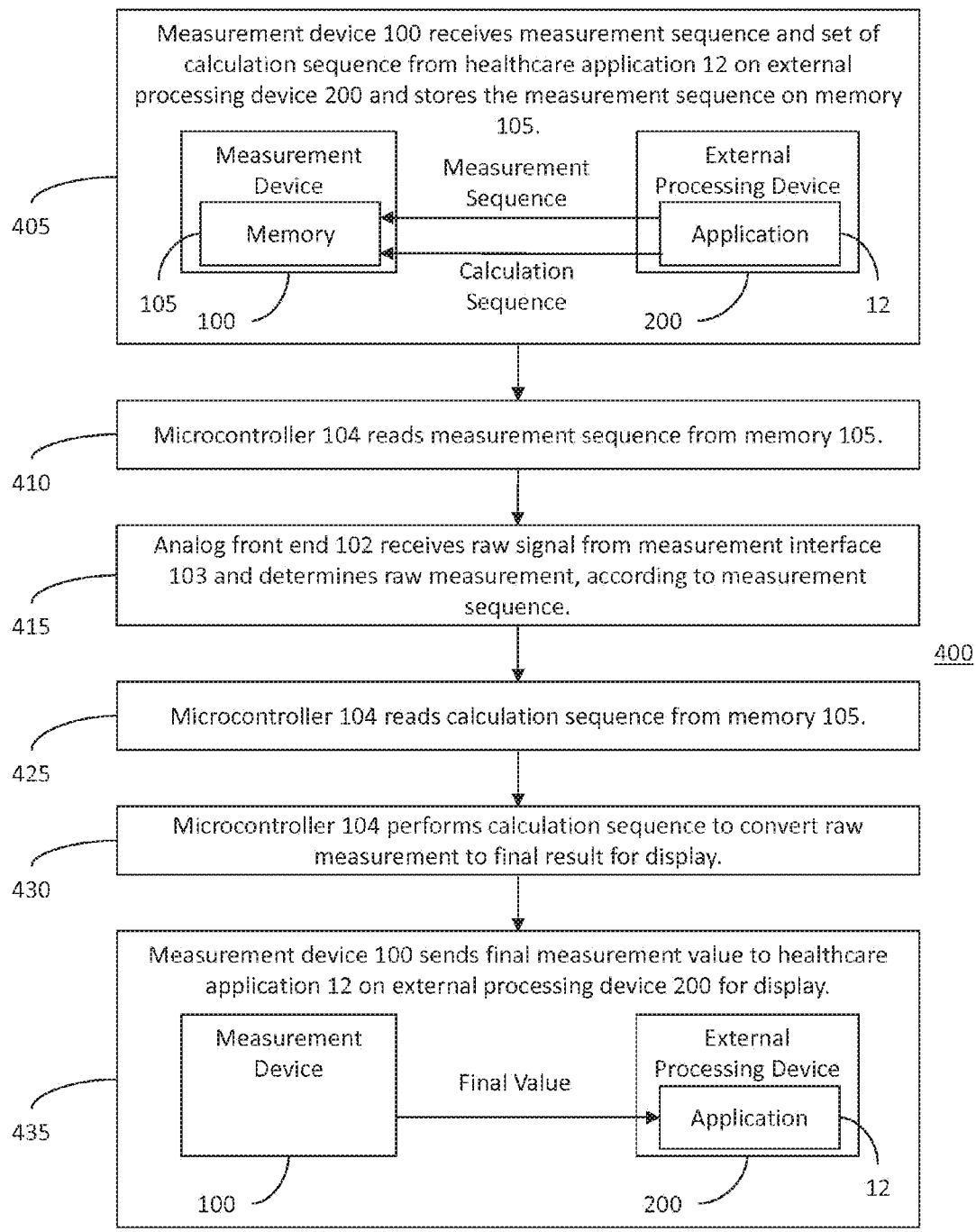
FIG. 4 illustrates another example approach for reconfiguring a measurement device, according to aspects of the present invention.

FIG. 4 illustrates another example approach 400 for reconfiguring the measurement device 100. In act 405, the measurement device 100 receives a measurement sequence and a calculation sequence from the healthcare application 12 residing on the external processing device 200 and stores the measurement sequence and the calculation sequence on the memory 105. As described above, the measurement sequence determines how the actual electrochemical or optical measurement is performed with the measurement interface 103 and how the raw electrochemical or optical signal is determined by the analog front end 102. Meanwhile, the calculation sequence converts the raw measurement data into a final measurement value (e.g., blood glucose concentration expressed as milligrams per deciliter (mg/dL)) that can be communicated to the user. The main microcontroller 104 reads the measurement sequence stored on the memory 105 in act 410. In act 415, the analog front end 102 receives the raw signal from the measurement interface 103 and the raw measurement data is determined according to the measurement sequence. In act 425, the measurement device 100 reads the calculation sequence from the memory 105. Thus, unlike the approach 300 of FIG. 3, the measurement device 100 in act 430 processes the raw measurement data to determine the final measurement value (e.g., blood glucose concentration expressed as milligrams per deciliter (mg/dL)). In act 435, the measurement device 100 sends the final measurement value to the healthcare application 12 residing on the external processing device 200, and the healthcare application 12 communicates the final measurement value to the user, e.g., via the display 208.

In the approach 400 of FIG. 4, the measurement device 100 is responsible for processing both the measurement sequence and the calculation sequence to determine the final measurement value. In the approach 300 of FIG. 3, however, the measurement device 100 receives the measurement sequence from the external processing device 200 while the calculation sequence remains on the external processing device 200. As such, the processing required for determining the final measurement value is distributed between the measurement device 100 and the external processing device 200. The approach 300 requires less processing power from the measurement device 100 and relies more on the processing power of the external processing device 200. Generally, the approach 300 takes advantage of the greater processing power of the external processing device 200 and allows the measurement device 100 to be manufactured with lower-power and lower-cost processors. The external processing devices, e.g., smart devices, can accommodate more complex calculation sequences that require greater processing power. Thus, future rollouts of calculation sequences are less likely to be constrained by a lack of processing power. Although the approach 300 shown in FIG. 3 may process the measurement sequence on the measurement device 100 and the calculation sequence on the external processing device 200, it is understood that the processing of instructions to determine the final measurement value may distributed between the devices in any manner. For example, some aspects of the calculation sequence may be processed on the measurement device 100 before data is sent to the external processing device 200 to complete the calculation sequence.

Because the external processing device 200 can be communicatively coupled to resources on an external network 20, the external processing device 200 can receive the measurement sequence and/or the calculation sequence from an external source, e.g., healthcare platform server 30. Furthermore, because the external processing device 200 can be communicatively coupled to the measurement device 100, the measurement device 100 can in turn receive the measurement sequence and/or the calculation sequence from the external source. According to aspects of the present invention, the measurement device 100 can be reconfigured to employ any measurement sequence and/or any calculation sequence received at any time from an external source, e.g., the healthcare platform server 30, on the external network 20. Thus, the measurement 100 is dynamically reconfigurable according to data received from an external source via the external processing device 200.

Figure 5:
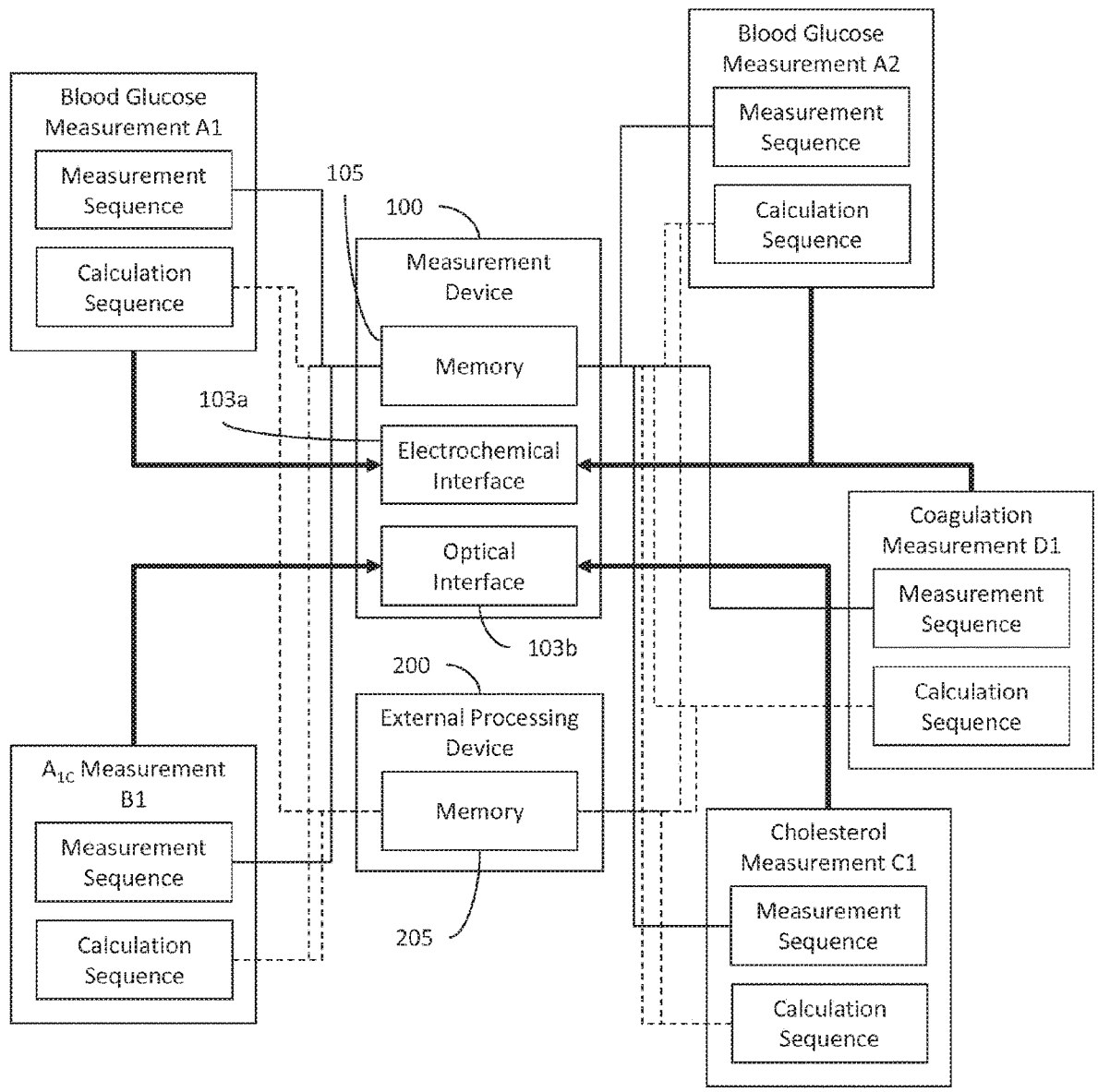
FIG. 5 illustrates an example system employing a reconfigurable measurement device according to aspects of the present invention.

In some embodiments, the memory 105 of the measurement device 100 and/or the memory 205 of the external processing device 200 may store the respective measurements sequence and/or the respective calculation sequences for measuring more than one type of health data. For example, as shown in FIG. 5, the memory may store a measurement sequence A1 and a calculation sequence A1 that can be used to configure the measurement device 100 to take blood glucose measurements. Additionally, the memory may store a measurement sequence B1 and a calculation sequence B1 that can be used to configure the measurement device 100 to take $A_{1C}$ measurements. Also, the memory may store a measurement sequence C1 and a calculation sequence C1 that can be used to configure the measurement device 100 to take cholesterol measurements. Furthermore, the memory may store a measurement sequence D1 and a calculation sequence D1 that can be used to configure the measurement device 100 to take coagulation (PT/INR) measurements. Indeed, the memory may store a measurement sequence A2 and a calculation sequence A2 that can be used to configure the measurement device 100 to take blood glucose measurements according to another process (e.g., using another type of test sensor to receive a fluid sample in the measurement interface 103). Thus, a user can select any of a plurality of measurement sequences and/or calculation sequences, e.g., via the healthcare application 12, to reconfigure the measurement device 100 to measure any of a plurality of health data. In other words, the reconfigurable measurement device 100 accommodates multi-chemistry measurements. As described above, the selected measurement sequence and calculation sequence can be stored on the memory 105 and processed on the measurement device 100. Alternatively, the selected measurement sequence can be on the memory 105 and processed on the measurement device 100 while the selected calculation sequence can be stored on the memory 205 of the external processing device 200 and processed on the external processing device 200. (The dotted lines of FIG. 5 indicate that the calculation sequences can be optionally stored on the measurement device 100 or the external processing device 200.)

Any number of the plurality of selectable measurement sequences and calculation sequences can be pre-stored on the memory 105 and/or the memory 205 for immediate availability and selection reconfigure the measurement device 100. These measurement sequences and calculation sequences can be selectively or automatically updated by accessing an external source, e.g., the healthcare platform server 30, via the network interface 210. Alternatively or additionally, any number of the selectable measurement sequences and calculation sequences can be made available on demand by accessing an external source, e.g., the healthcare platform server 30 at the time of reconfiguration.

As described above, the at least one measurement interface 103 on the measurement device 100 may accommodate more than one sensing technology, e.g., electrochemical or optical sensing. Thus, referring to FIG. 5, it is also contemplated that any number of the plurality of selectable measurement sequences and calculation sequences can be employed with the electrochemical measurement interface 103a, while any number of the plurality of selectable measurement sequences and calculation sequences can be employed with the optical measurement interface 103b. As shown in FIG. 5, for example, the blood glucose measurements A1 and A2 and the coagulation measurement D1 are achieved with the electrochemical measurement interface 103a. Meanwhile, the $A_{1C}$ measurement B1 and the cholesterol measurement C1 are achieved with the optical measurement interface 103b.

While the invention is susceptible to various modifications and alternative forms, specific embodiments and methods thereof have been shown by way of example in the drawings and are described in detail herein. It should be understood, however, that it is not intended to limit the invention to the particular forms or methods disclosed, but, to the contrary, the intention is to cover all modifications, equivalents and alternatives falling within the spirit and scope of the invention.

What is claimed is:

1. A system for measuring health data, comprising:
    a measurement device including:
        at least one measurement interface configured to receive a first fluid sample and a second fluid sample;
        at least one processor configured to measure a first characteristic of the first fluid sample received by the at least one measurement interface and a second characteristic of the second fluid sample received by the at least one measurement interface, the first characteristic relating to a blood glucose measurement, the second characteristic relating to an $A_{1c}$ measurement, a coagulation measurement, or a cholesterol measurement;
        at least one memory device configured to store firmware, first algorithm data, and second algorithm data, the first algorithm data including instructions for obtaining the first characteristic from the first fluid sample, the second algorithm data including instructions for obtaining the second characteristic from the second fluid sample, the first algorithm data and from the second algorithm data,
        wherein the firmware is configured to interface with various sensors on the measurement device as instructed by one of the first algorithm data or the second algorithm data for obtaining one of the first characteristic or the second characteristic;

a wireless microcontroller configured to receive and send communications to an external computing device;

the external computing device comprising an external device memory and at least one external device processor, the at least one external device processor executing an application providing a user interface to a user for remotely controlling operation of the measurement device, wherein responsive to receiving a first user selection from the external computing device to measure the first characteristic of the first fluid sample via the wireless microcontroller, the external computing device transmits the first algorithm data to the measurement device and the at least one processor executes the firmware with the first algorithm data to measure the first characteristic of the first fluid sample, and wherein responsive to receiving a second user selection from the external computing device to measure the second characteristic of the second fluid sample via the wireless microcontroller, the external computing device transmits the second algorithm data to the measurement device and the at least one processor executes the firmware with the second algorithm data instead of the first algorithm data to reconfigure the measurement device to measure the second characteristic of the second fluid sample.

2. The system of claim 1, wherein the measurement device further includes an analog front end coupled to the at least one measurement interface and the at least one processor, the first algorithm data including a first measurement sequence with instructions for obtaining a first raw measurement signal from the first fluid sample, and the second algorithm data including a second measurement sequence with instructions for obtaining a second raw measurement signal from the second fluid sample, the at least one measurement interface being configured to obtain the first raw measurement signal based on the first fluid sample according to the first measurement sequence, the analog front end being configured to receive the first raw measurement signal from the at least one measurement interface according to the first measurement sequence, and when the measurement device is reconfigured, the at least one measurement interface being configured to obtain the second raw measurement signal based on the second fluid sample according to the second measurement sequence, the analog front end being configured to receive the second raw measurement signal from the at least one measurement interface according to the second measurement sequence, the instructions for obtaining the first raw measurement signal from the first fluid sample being different than the instructions for obtaining the second raw measurement signal from the second fluid sample.

3. The system of claim 2, wherein the first algorithm data includes a first calculation sequence with instructions for converting the first raw measurement signal to a first measurement value, and the second algorithm data includes a second calculation sequence with instructions for converting the second raw measurement signal to a second measurement value, the at least one processor being configured to convert the first raw measurement signal to the first measurement value according to the first calculation sequence, and when the measurement device is reconfigured, the at least one processor being configured to convert the second raw measurement signal to the second measurement value according to the second calculation sequence, the instructions for converting the first raw measurement signal to the first measurement value being different than the instructions for converting the second raw measurement signal to the second measurement value.

4. The system of claim 1, wherein the at least one memory device is further configured to store at least one of software, program parameters, calibration data, or lookup tables.

5. The system of claim 1, further comprising an ftfl external processing device configured to be communicatively coupled to the measurement device and to execute a healthcare application that communicates with the measurement device.

6. The system of claim 5, wherein the ftfl external processing device and the measurement device are wirelessly coupled.

7. The system of claim 5, wherein the ftfl external processing device is a smart device.

8. The system of claim 5, wherein the healthcare application communicates the first algorithm data or the second algorithm data for storage on the at least one memory device of the measurement device.

9. The system of claim 8, wherein the ftfl external processing device is coupled to an external data source via a network, the external data source communicating the first algorithm data or the second algorithm data to the healthcare application for further communication to the measurement device.

10. The system of claim 4, wherein the measurement device communicates the first characteristic or the second characteristic to the application for display on a display of the external computing device.

11. The system of claim 2, further comprising an external processing device configured to be communicatively coupled to the measurement device and to execute a healthcare application that communicates with the measurement device, the measurement device sending the first raw measurement signal and the second raw measurement signal to the healthcare application, the external processing device storing a first calculation sequence and a second calculation sequence, the healthcare application converting the first raw measurement signal to a first measurement value according to the first calculation sequence and converting the second raw measurement signal to a second measurement value according to the second calculation sequence, and the healthcare application displaying the first measurement value and the second measurement value on a display of the external processing device.

12. The system of claim 3, further comprising an external processing device configured to be communicatively coupled to the measurement device and to execute a healthcare application that communicates with the measurement device, the measurement device sending the first measurement value and the second measurement value to the healthcare application, and the healthcare application displaying the first measurement value and the second measurement value on a display of the external processing device.

13. The system of claim 1, wherein the at least one measurement interface includes a plurality of measurement interfaces, and the measurement device is configured to receive a fluid sample via any one of the plurality of measurement interfaces.

14. The system of claim 13, wherein the first algorithm data configures the measurement device to receive the first fluid sample via one of the plurality of measurement interfaces and the second algorithm data configures the measurement device to receive the second fluid sample via another of the plurality of measurement interfaces.

15. The system of claim 13, wherein the plurality of measurement interfaces includes an electrochemical measurement interface and an optical measurement interface.

16. The system of claim 13, wherein one or more of the plurality of measurement interfaces is reconfigurable to receive fluid samples for at least one of the blood glucose measurement, the A1c measurement, the coagulation measurement, or the cholesterol measurement.

17. The system of claim 1, wherein the at least one measurement interface is a single measurement interface that receives both the first fluid sample and the second fluid sample.

18. The system of claim 1, wherein the first characteristic cannot be obtained using the second algorithm data and the second characteristic cannot be obtained using the first algorithm data.

19. A system for measuring health data, comprising:
an external processing device including:
at least one external processor;
an external memory device storing a measurement sequence and a calculation sequence; and
a reconfigurable measurement device communicatively coupled to the external processing device, the reconfigurable measurement device including:
a measurement interface configured to obtain a fluid sample via a test sensor;
a measurement memory device storing firmware and being configured to receive the measurement sequence from the external memory device of the external processing device in response to a user selection to measure a characteristic of the fluid sample,
wherein the firmware is configured to interface with the test sensor as instructed by the measurement sequence from the external memory device of the external processing device;
wherein the user selection is received at the external processing device; and
at least one measurement processor configured to (i) read the measurement sequence from the measurement memory device of the reconfigurable measurement device, (ii) execute the firmware with the measurement sequence to obtain a raw measurement signal from the measurement interface based on the fluid sample received by the test sensor and (iii) cause the raw measurement signal to be transmitted to the external processing device,
wherein the external memory device of the external processing device is configured to receive the raw measurement signal from the reconfigurable measurement device, and
wherein the at least one external processor of the external processing device is configured to (i) read the calculation sequence from the external memory device of the external processing device, and (ii) execute the calculation sequence to convert the raw measurement signal to a measurement value of the characteristic of the fluid sample.

20. A system for measuring health data, comprising:
an external processing device including:
at least one processor; and
a memory device storing instructions for:
a first measurement sequence that includes instructions for:
obtaining a first raw measurement signal,
a first calculation sequence that includes instructions for converting the first raw measurement signal to a measurement value of a first characteristic,
a second measurement sequence that includes instructions for obtaining a second raw measurement signal by a second test sensor via firmware, the instructions for obtaining the first raw measurement signal being different than the instructions for obtaining the second raw measurement signal, and
a second calculation sequence that includes instructions for converting the second raw measurement signal to a measurement value of a second characteristic, the instructions for converting the first raw measurement signal to the measurement value of the first characteristic being different than the instructions for converting the second raw measurement signal to the measurement value of the second characteristic; and
a reconfigurable measurement device configured to be communicatively coupled to the external processing device, the reconfigurable measurement device including:
a measurement interface configured to receive (i) a first fluid sample via a first test sensor at a first time and (ii) a second fluid sample via the second test sensor at a second time after the first time;
a measurement memory device storing the firmware; and a processor,
wherein the firmware is configured to interface with the second test sensor as instructed by the second measurement sequence,
wherein in response to a first user selection for a measurement value of the first characteristic received at the external processing device:
the measurement memory device of the reconfigurable measurement device is configured to receive and store the first measurement sequence and the first calculation sequence from the memory device of the external processing device, and sample received by the measurement interface and convert the first raw measurement signal to the measurement value of the first characteristic of the first fluid sample received by the measurement interface, the first characteristic relating to a blood glucose measurement, and
wherein in response to a second user selection for a measurement value of the second characteristic received at the external processing device:
the measurement memory device of the reconfigurable measurement device is configured to receive and store the second measurement sequence and the second calculation sequence from the memory device of the external processing device, and
the processor of the reconfigurable measurement device is configured to (i) read the second measurement sequence and the second calculation sequence from the measurement memory device of the reconfigurable measurement device, (ii) execute the firmware as instructed by the second measurement sequence and the second calculation sequence to obtain the second raw measurement signal from the second fluid sample received by the measurement interface and convert the second raw measurement signal to the measurement value of the second characteristic of the second fluid sample received by the measurement interface, the second characteristic relating to an A1c measurement, a coagulation measurement, or a cholesterol measurement.

* * * * *